United States Patent [19]

Nash et al.

[11] 4,252,898
[45] Feb. 24, 1981

[54] ANTIBIOTICS A6888C AND A6888X

[75] Inventors: Stephen M. Nash, Greenwood; Kay F. Koch, North Salem; Marvin M. Hoehn, Indianapolis, all of Ind.

[73] Assignee: Eli Lilly and Company, Indianapolis, Ind.

[21] Appl. No.: 41,580

[22] Filed: May 23, 1979

[51] Int. Cl.³ .............................................. C12P 19/62
[52] U.S. Cl. .................................. 435/76; 536/17 R; 435/886
[58] Field of Search ........................................ 435/76

[56] References Cited

U.S. PATENT DOCUMENTS 3,159,540  12/1964  Kawaguchi et al. ............. 435/128 X
3,950,516  4/1976   Miyaki ................................ 424/123

OTHER PUBLICATIONS

Omura et al., J. Antibiotics 28, 401–433, (Jun. 1975).
Keller–Schierlein in Fortschrittee der Chemie Organischer Naturstoffe, vol. 30, pp. 314–445, (p. 359 only checked).
Suzuki, Bull. Chem. Soc., Japan, vol. 48, p. 292, (1970).
Tsukira et al., J. Antibiotics, vol. 22, pp. 89–99, (1969).

Primary Examiner—Lionel M. Shapiro
Attorney, Agent, or Firm—Nancy J. Harrison; Arthur R. Whale

[57] ABSTRACT

Antibiotic compounds of the formula:

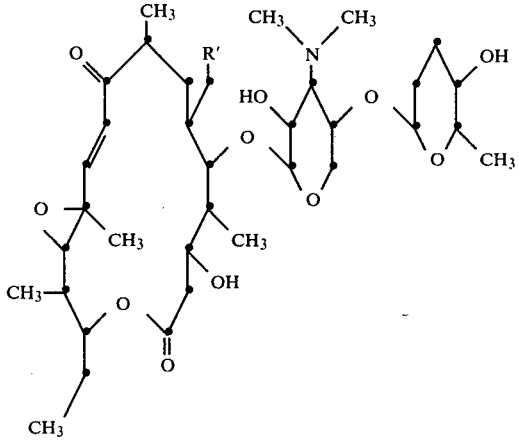

wherein R' is

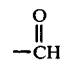

or —CH$_2$OH, and the non-toxic pharmaceutically acceptable acid addition salts thereof, are produced by culturing Streptomyces flocculus NRRL 11459. Techniques for isolating the compounds are also described. Cirramycin A$_1$ and cirramycin B are coproduced.

6 Claims, No Drawings

ANTIBIOTICS A6888C AND A6888X

This invention relates to new macrolide antibiotics and to methods of preparation thereof.

The antibiotic complex known as cirramycin and its preparation are disclosed in U.S. Pat. No. 3,159,540. The aforesaid patent also describes two factors isolated from the cirramycin complex-cirramycin A and cirramycin B. Other factors of the cirramycin complex are also known. Cirramycin B [which appears to be identical to cirramycin $B_1$, antibiotic B-58941 (Takeda), and acumycin (Ciba)] and cirramycin $A_1$ are described by S. Omura et al., *J. Antibiotics* 28, 401 (1975) and by W. Keller-Schierlein, "Chemie der Makrolid-Antibiotica", *Fortschritte Der Chemie Organischer Naturstoffe*, W. Hertz, H. Grisebach, and G. W. Kirby, Editors, Vol. 30, pages 314–445 (1973). U.S. Pat. No. 3,950,516 disclosed the preparation of cirramycin $A_1$ from cirramycin $B_1$ by incubation with cane molasses. The preparation of cirramycin $A_1$ from cirramycin $B_1$ by mild acid hydrolysis of cirramycin $B_1$ (Antibiotic B-58941, Takeda) is disclosed by T. Suzuki *Bull. Chem. Soc. Japan* 48, 292 (1970). Cirramycin $A_1$ is also described by H. Tsukira et al., *J. Antibiotics*, 22, 89 (1969).

The structural formulae of cirramycin $A_1$ and cirramycin B are depicted in Formula I shown below:

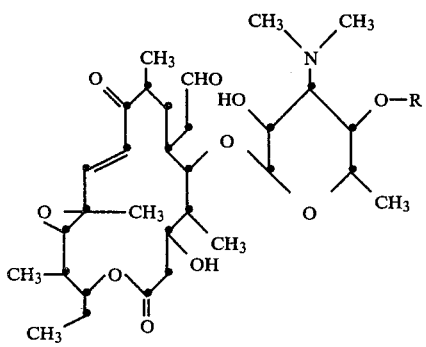

wherein:
(a) R is H (cirramycin $A_1$) and
(b) R is

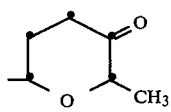

(cinnamycin B).

Cirramycin $A_1$ and cirramycin B are both produced by a strain of *Streptomyces cirratus*. Cirramycin B (Antibiotic B-58941, Takeda) is also produced by a strain of *Streptomyces fradiae*.

It has now been found that cirramycin $A_1$ and B and two new macrolide antibiotics, are coproduced by a strain of *Streptomyces flocculus*, designated NRRL 11459. The new antibiotic substances are related structurally to cirramycin $A_1$ and cirramycin B and have the structural formulae shown in Formula II:

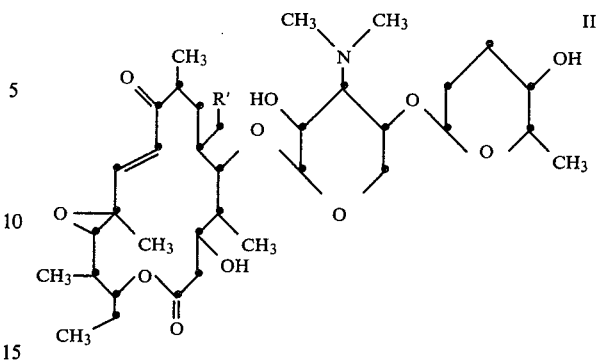

wherein:
(a) R' is

and
(b) R' is —$CH_2OH$

, or a non-toxic, pharmaceutically acceptable acid addition salt thereof.

In its composition of matter aspect, the invention sought to be patented comprehends the new antibiotic compounds of Formula II which are arbitrarily designated herein as Antibiotic A6888C (R' is —CHO) and Antibiotic A6888X (R' is —$CH_2OH$). Antibiotics A6888C and A6888X exhibit antibacterial activity, particularly against gram positive bacteria, in standard test procedures.

It will be apparent to those skilled in the art that the compounds of Formula II contain a tertiary aliphatic amino group which is capable of forming acid addition salts by reaction with an acid of suitable strength. For the biological purposes of this invention such salts must be non-toxic and pharmaceutically acceptable. However, it will be recognized that any salt can be used for the purposes of isolation and/or purification, provided such salt can be converted, when desired, to a non-toxic, pharmaceutically acceptable salt. Acids conventionally known to be useful for forming addition salts with an aliphatic tertiary amine may be used in this invention.

In its process aspect, this invention comprehends a method of preparing cirramycin $A_1$, cirramycin B, or a compound of Formula II (A6888C or A6888X) which comprises cultivating *Streptomyces flocculus* NRRL 11459 in a culture medium containing assimilable sources of carbon, nitrogen, and inorganic salts under submerged aerobic conditions until a substantial amount of each compound is produced.

The term "complex" as used in the fermentation art and in this specification and claims refers to a mixture of the coproduced individual antibiotic factors. As will be recognized by those skilled in the art, the number and ratio of individual factors present in an antibiotic complex produced by a particular organism will vary depending upon the fermentation conditions used. "A6888 complex" means the complex comprising Antibiotic A6888C, Antibiotic A6888X, cirramycin $A_1$ and cirramycin B. Cirramycin $A_1$ and cirramycin B are also referred to herein as Antibiotics A6888F and A6888A, respectively.

The organism used to produce the A6888 complex is a strain of *Streptomyces flocculus* isolated from a soil sample from Wyoming, U.S.A. The strain has been deposited with the permanent culture collection of the Northern Utilization Research and Development Division, Agriculture Research Service, United States Department of Agriculture, Peoria, Ill. Its accession number in this collection in NRRL 11459.

CHARACTERIZATION OF *STREPTOMYCES FLOCCULUS* NRRL 11459

The NRRL 11459 culture employed to prepare the A6888 complex has been classified as a strain of *Streptomyces flocculus* (Duché) Waksman and Henrici. The similarties and differences between the NRRL 11459 culture and the published culture can be summarized briefly as follows:

| Similarities | Differences |
| --- | --- |
| morphology | utilization of rhamnose |
| spore surface | flocculus appearance |
| aerial spore mass | production of ferrioxamine E |
| color | |
| growth on selected media | |
| melanoid pigment production | |
| reverse colony color | |
| lack of soluble pigments | |
| carbon utilization | |

The methods employed for the characterization are those recommended for the *International Streptomyces Project* for the characterization of Streptomyces species [E. B. Shirling and D. Gottlieb. *Intern. Journal of Systematic Bacteriol.*, 16, 313 (1966)]. Certain supplementary tests have also been employed. Color names are assigned according to the Inter-Society Color Council-National Bureau of Standards [ISCC-NBS) method [K. Kelly and B. Judd, *The ISCC-NBS Methods of Designating Color and a Dictionary of Color Names*, U.S. Department of Commerce, Circ. 553, Washington, D.C. 1955. Figures in parenthesis refer to the Tresner and Backus color series [H. D. Tresner and E. J. Backus, *Appl. Microb.* 11, 335 (1961)]. Color tab designations are underlined. The Maerz and Paul color blanks are entered in brackets. [A. Maerz and M. Paul, *Dictionary of Color*, McGraw Hill Book Company, Inc., N.Y. 1950]. Carbon utilization is determined on ISP #9 basal medium to which carbon sources are added to equal a final concentration of 1.0%. The carbon sources are sterilized by filtration; the basal medium by autoclaving. Plates are read after 14 days incubation at 30° C.

The cell wall sugars are determined using a modification of the procedure of M. Lechevalier, "Chemical Methods as Criteria for the Separation of Actinomycetes Into Genera", workshop sponsored by the subcommittee on Actionomycetes of the American Society of Microbiology, Dr. Thoman G. Pridham, Convenor, held at the Institute of Microbology, Rutgurs University, New Brunswick, N.J., 1971. The isomer of diaminopimelic acid is determined using the method of B. Becker *Appl. Microbiol.*, 11 421 (1946). Amino acid analysis is determined with washed cell wall fragments. Melanoid pigments are determined using ISP #6 (peptone-yeast extract iron agar) and ISP #7 (tyrosine agar). Inhibitors are tested by incorporating varing concentrations of inhibitors into ISP #2 agar plates and streaking the culture on the surface. Starch hydrolysis is determined by testing for the presence of starch with iodine on ISP #4 agar plates. Temperature range, NaCl tolerance, pH range, and antibiotic sensitivity are done using ISP #2 agar medium. The range of temperatures are: 25°, 28°, 30°, 34°, 37°, 40°, 45°, 50°, 55° C. NaCl tolerance is measured by adding NaCl to the agar to equal: 0, 1, 2, 3, 4, 5, 6, 8, 10, 12% and incubating at 30° C. for 7 days. Antibiotic sensitivity is determined using sensitivity discs padded onto seeded agar plates of ISP #2 medium and incubating at 30° C. for 14 days.

The results of the taxonomic studies are summarized below:

| MORPHOLOGY | |
| --- | --- |
| NRRL 11459 | *S. flocculus* |
| Sporophores (S) spiralled, with some (RA), wide open hooks and loops. Observed on ISP #3 Chains of spores >10. | Sporophores (S) spiralled with some loops, partial spirals or hooks. Observed on ISP #3 Short chains of 3–10 spores on partial spirals and hooks Long chains of spores >10 |
| Spore surface as determined by scanning electron microsocopy is smooth. | Spore surface as determined by electron microscopy is smooth. |
| Spore size: range = 1.3–1.95 × 0.65–0.97 μM average = 1.72 × 0.91 μM shapes = oblong | Spore size: (size not given) shape = oblong |

| CULTURAL CHARACTERISTICS | | |
| --- | --- | --- |
| Medium | NRRL 11459 | *S. flocculus* |
| ISP #2 | G abundant | weak |
| | R [13K6] light yellowish brown | pale grayish yellow |
| | Am poor. (Y) 2ba pale yellow | poor. (Y) 2ba pale yellow |
| | SP none | none |
| ISP #3 | G fair | good |
| | R [11B1] pale yellow | pale grayish yellow |
| | Am fair. (Y) 2ba pale yellow | good. (Y) 2ba pale yellow |
| | SP none | none. |
| ISP #4 | G good | weak |
| | R [10G3] light yellow | pale grayish yellow |
| | Am fair. (Y) 2ba pale yellow | poor. (Y) 2ba pale yellow |
| | SP none | none |
| ISP #5 | G poor | weak |
| | R clear | pale grayish yellow |
| | Am none | poor. (Y) 2ba pale |

-continued

| CULTURAL CHARACTERISTICS | | | |
|---|---|---|---|
| Medium | | NRRL 11459 | S. flocculus |
| TPO | SP | none | yellow |
| | G | good | none |
| | R | [11H2] light yellow | (not given) |
| | Am | abundant. (Y) 2ba pale yellow | |
| | Sp | slight dark brown | |
| | B | poor | (not given) |
| Glucose Asparagine | R | clear | |
| | Am | none | |
| | SP | none | |
| Bennetts | G | abundant | (not given) |
| | R | [11J2] light yellow | |
| | Am | fair. (Y) 2ba pale yellow | |
| | Sp | none | |
| Czapek's | G | good | (not given) |
| | R | [12C2] grayish yellow | |
| | Am | poor (Y) ldb grayish yellow | |
| | SP | none | |

G = growth; R = reverse; Am = aerial myceliumSP = soluble pigment

| PHYSIOLOGICAL CHARACTERISTICS Carbon utilization: | | |
|---|---|---|
| Substrate | NRRL 11459 | S. Flocculus |
| L-Arabinose | + | + |
| D-Fructose | + | + |
| D-Galactose | + | + |
| i-Inositol | + | + |
| D-Mannitol | + | + |
| D-Raffinose | + | + |
| L-Rhamnose | + | − |
| Salicin | ± | + |
| Sucrose | + | + |
| D-Xylose | + | + |
| D-Glucose | + | + |
| Adonitol | − | |
| Arabic acid | + | |
| D(−)Arabinose | − | |
| D(+)Arabitol | + | |
| L(−)Arabitol | − | |
| D(+)Cellobiose | + | |
| α-Cellulose | − | |
| Chitin | − | |
| Dulcitol | − | |
| i-Erythritol | − | |
| Esculin hydrate | − | |
| Fructose | + | |
| α-D(+)Fucose | − | |
| α-L(−)Fucose | − | |
| D(+)Glucosamine | + | |
| αMe-D-Glucoside | + | |
| βMe-D-Glucoside | + | |
| Glycerol | + | |
| Inulin | + | |
| D(+)Lactose | + | |
| D(+)Maltose | + | |
| D(+)Mannose | + | |
| αMe-D-Mannoside | + | |
| αMe(+)Melibiose | + | |
| D(+)Melizitose | − | |
| Palatinose | + | |
| Pectin | + | |
| D(−)Ribose | + | |
| D(−)Sorbitol | − | |
| L(−)Sorbose | − | |
| Starch | + | |
| D(−)Tagatose | − | |
| D(+)Trehalose | − | |
| D(+)Turanose | + | |
| Xylan | + | |
| αMe-D-Xyloside | − | |
| βMe-D-Xyloside | − | |
| Xylitol | − | |
| Sodium Acetate | − | |
| Sodium Butyrate | − | |
| Casein (EHC) | + | |
| Sodium Citrate | + | |

| PHYSIOLOGICAL CHARACTERISTICS Carbon utilization: | | |
|---|---|---|
| Substrate | NRRL 11459 | S. Flocculus |
| Sodium Fumerate | + | |
| Calcium Lactate | − | |
| Sodium Propionate | − | |
| Sodium Pyruvate | + | |
| Sodium Succinate | + | |

Key:
+ = positive utilization
− = negative utilization
± = partial, doubtful utilization

| Antibiotic Sensitivity | | | |
|---|---|---|---|
| Antibiotic | Conc/Disc | Class | NRRL 11459 |
| Erythromycin | 15 μg | macrolide | + |
| Keflin | 30 μg | β-Lactam | − |
| Lincomycin | 2 μg | glycoside | + |
| Nystatin | 100 units | polyene | − |
| Polymixin B | 300 units | peptide | + |
| Streptomycin | 10 μg | aminoglycoside | + |
| Tetracycline | 30 μg | tetracycline | + |
| Vancomycin | 30 μg | glycoside | + |

Key:
+ = sensitive (zones of inhibition)
− = resistat (no zones of inhibition)

| Inhibitor Sensitivity | |
|---|---|
| Inhibitor | MIC μg./ml. |
| Antimony Potassium tartrate | 250 |
| Bismuth Citrate | >500 |
| Crystal Violet | 1 |
| Potassium Tellurite | >500 |
| Pyronin B | 250 |
| Safranin | 10 |
| Sodium Azide | 10 |
| Sodium Selenite | 25 |
| Thallium Acetate | <10 |

| Additional Physiological Characteristics | |
|---|---|
| Characteristic | NRRL 11459 |
| Melanoid pigment | |
| ISP #1 | − |
| ISP #6 | − |
| ISP #7 | − |

-continued

| Additional Physiological Characteristics | | |
|---|---|---|
| Characteristic | NRRL 11459 | |
| Gelatin liquefaction | − | |
| Skim Milk | − | |
| Starch hydrolysis | + | |
| Carrot/potato plugs | + | |
| Temperature range | 25–30° C. | (partial at 40° C.) |
| Nitrate reduction | − | |
| NaCl tolerance; growth up to | 4% | (partial at 6%) |
| Oxidase | − | |
| Catalase | + | |
| Phosphatase | + | |
| DN'ase | + | |
| Urease | + | |

CELL WALL CONSTITUENTS

Major constituents of the cell wall are: LL-DAP and glycine. Alanine, glutamic acid and glucosamine are present, but these are present in all cell wall preparations. Sugar analysis shows glucose present and traces of galactose and mannose. This information indicates a Type I cell wall, and a type C sugar pattern.

As is the case with other organisms the characteristics of *Streptomyces flocculus* NRRL 11459, are subject to variation. For example, artifical variants and mutants of the strain may be obtained by treatment with various known mutagens such as X-rays, high-frequency rays, radioactive rays, and chemicals. All natural and artifical variants and mutants of *Streptomyces flocculus* NRRL 11459 which are capable of producing the compounds of Formula II may be used in the processes of this invention.

The medium employable to cultivate *Streptomyces flocculus* NRRL 11459 can be any one of several media. However, for economy of production, maximum yield of antibiotic, and ease of isolation of the antibiotic, certain culture media containing relatively simple nutrient sources are preferred. Thus, for example, glucose and dextrin are preferred sources of carbohydrate, although fructose, sucrose, mannitol, starch and the like can also be employed. Preferred sources of nitrogen include corn steep liquor, acid-hydrolyzed casein, soybean grits and the like.

Nutrient inorganic salts to be incorporated in the culture media can include the customary salts capable of yielding sodium, potassium, iron, magnesium, ammonium, calcium, phosphate, chloride, sulfate and like ions. Additionally, sources of growth factors such as distillers' solubles and yeast extracts can be beneficial.

As is necessary for the growth and development of other microorganisms, essential trace elements should also be included in the culture medium for growing the actinomycete employed in this invention. Such trace elements are commonly supplied as impurities incidental to the addition of other constituents to the media.

The initial pH of the culture medium can be varied widely. However, it has been found desirable that the initial pH of the medium be between about 6.5 and about 7.5. A pH of about 7.0 is preferred.

Submerged, aerobic cultural conditions are the conditions of choice for the cultivation. For the production of relatively small amounts, shake flasks can be employed; but for the preparation of large amounts, submerged aerobic culture in sterile tanks is preferred. The medium in the sterile tank can be inoculated with a sporulated suspension, but, because of the growth lag experienced when a sporulated suspension is used as the inoculum, the vegetative form of the culture is preferred. By thus avoiding the growth lag, more efficient use of the fermentation equipment is realized. Accordingly, it is desirable first to produce a vegetative inoculum of the organism by inoculating a relatively small quantity of culture medium with the spore form of the organism, and when a young, active vegetative inoculum has been obtained, to transfer the vegetative inoculum aseptically to the large tank. The medium in which the vegetative inoculum is produced can be either the same as, or different from, the medium utilized for the large scale production.

The organism produces A6888C at temperatures in the range of about 23° C. to about 32° C. Optimal production of A6888C appears to occur at temperatures of about 25°–28° C.

The relative amounts of the individual factors produced is strongly dependent upon the fermentation time. In general, increasing the time promotes the relative amounts of A6888C and A6888X in relation to the amounts of cirramycin $A_1$ and cirramycin B. A time of from about 90 to about 115 hours provides maximum amounts of A6888C and A6888X and minimal amounts of cirramycin $A_1$ and cirramycin B. A time of from about 40 to about 60 hours affords maximum amounts of cirramycin $A_1$ (A6888F) and cirramycin B (A6888A).

The individual factors are removed and isolated from the fermentation broth by conventional techniques, such as solvent extraction, counter current distribution, and chromatography. It should be recognized that in order to obtain sufficient amounts of the factors for characterization, whole broths from several tank fermentations may be combined for work-up. In addition, chromatographic fractions obtained from two or more purifications carried out using similar techniques can be compared by tlc analysis and, if shown to be identical, can be combined, and the combined sample can be employed for further purification and separation.

The preferred general method for recovering A6888C, A6888X, cirramycin $A_1$, and cirramycin B from fermentation media is described as follows:

The fermentation broth is adjusted to pH 3.0 to 3.5 and filtered to remove mycelia. The broth filtrate at the same pH range is extracted with ethyl acetate (or other suitable organic solvent) to remove most of the bulk inactive substances. The antibiotic substances present in the aqueous phase are then removed by adjusting the pH to about 7 and extracting the aqueous medium with ethyl acetate (or other suitable solvent). The ethyl acetate is evaporated and a crude, dry antibiotic preparation is obtained. This material is further purified by counter current distribution (CCD) using bensene-Sorenson's buffer (pH 5.8) as the solvent system. The benzene phases from the CCD are each evaporated to dryness. The aqueous phases from the CCD are each extracted consecutively with benzene and ethyl acetate. The organic solvents from the solvent extractions are separated and evaporated. The residues obtained from each CCD phase are then analyzed by tlc and bioautography. The residues shown to contain the desired factors by tlc are dissolved in chloroform and pooled.

The individual factors are separated and isolated by high performance liquid chromatography (HPLC) on silica gel (Quantum LP-1) using a dry-packed column and a linear gradient eluent system of chloroform to chloroform-methanol (9:1, v:v), each containing 0.01% added ethanolamine. The fractions are analyzed by tlc and bioautography. Those fractions having a similar composition are pooled, and those samples which are shown to contain impurities or to contain more than one factor may be rechromatographed using HPLC under the conditions above-described. Using this chromatographic method of separation, each individual factor (A6888C, A6888X, cirramycin A₁ and cirramycin B) is obtained in highly pure form.

The methods of making and using the invention are illustrated in the following Examples.

EXAMPLE 1

The *Streptomyces flocculus* NRRL 11459 culture is prepared and maintained on an agar slant having the following composition:

|  |  |
|---|---|
| Glucose | 0.5% |
| Yeast extract | 0.2 |
| CaCO₃ | 0.3 |
| Agar | 2.0 |
| Vegetable juice* | 20.0 |
| Deionized water | q.s. |

*V-8 Juice, Campbell Soup Company, Camden, N.J.

The pH of the medium is 6.1; after sterilization, pH 5.9.

The slant is inoculated with the organism and is incubated at 30° C. for 7 days. The sporulated slant is flooded with calf's serum and gently scraped to give an aqueous spore suspension. The suspension is transferred to small tubes and lyophilized for preservation. One lyophilized pellet is used to inoculate a 250 ml Erlenmeyer flask containing 50 ml of a vegetative culture medium having the following composition:

|  |  |
|---|---|
| Glucose | 1.5% |
| Soybean grits | 1.5 |
| Corn steep liquor | 1.0 |
| NaCl | 0.5 |
| CaCO₃ | 0.2 |
| Tap water | q.s. |

The pH of the medium is adjusted to 6.5 with 5 N sodium hydroxide; after sterilization, the pH is 7.0. The inoculated medium is incubated for 48 hours at 30° C. on a rotary shaker operating at 250 rpm. A 10 ml portion of the resulting culture is then employed to inoculate each of two 2 liter flasks containing 400 ml of sterilized second stage growth medium having the same composition as that described above. The inoculated medium is incubated for 24 hours at 30° C. on a rotary shaker operating at 250 rpm.

An 800 ml. portion of the second-stage medium is used to inoculate 100 liters of the following medium in a 165-liter tank fermentor:

|  |  |
|---|---|
| Glucose | 1.5% |
| Soybean grits | 1.5 |
| Acid hydrolyzed casein | 0.1 |
| Casein | 0.3 |
| CaCO₃ | 0.25 |
| Tap water | q.s. to 100 liters |

The pH of the medium is adjusted to 7.4 with 5 N sodium hydroxide. After sterilization the pH is 7.2. The inoculated medium is aerated at a rate of 0.5 volume of air per volume of culture per minute and is stirred with conventional agitators at 300 rpm. The fermentation is carried out at 25° C. for 90 hours. The production of biological activity is monitered by turbidimetric assay using *Staphylococcus aureus* as the test organism. The composition of the biologically active substances is monitered by tlc, for example, by using silica gel plates developed in $CHCl_3$-methanol (3:1, v:v) and the factors are determined by bioautography vs. a microorganism such as *Micrococcus luteus*.

EXAMPLE 2

The whole fermentation broth (380 L.) from four fermentations (each carried out according to Example 1) is adjusted to pH 3.0–3.5 with 5 N sulfuric acid and the broth is filtered in the presence of a filter aid (HYFLO Super Cel-Johns Manville) to remove the mycelial mass. The filtered broth (280 L.) at pH 3.0–3.5 is then extracted two times with ethyl acetate (122 liters and 135 liters, respectively). The aqueous phase (295 L.) is adjusted to pH 7.0 and extracted once with ethyl acetate (195 L.). The ethyl acetate phase (190 L.) is concentrated to give a dry crude material (12.7 g.). This material, dissolved in a mixture of benzene (1 L.) and Sorenson's citrate buffer (pH 5.8) (1 L.), is subjected to a counter current distribution utilizing five separatory funnels with benzene and Sorenson's citrate buffer (pH 5.8) as the extraction solvents. The benzene phases are evaporated to dryness and lyophilized. The buffer aqueous phases are extracted with benzene and ethyl acetate, and the organic phases are removed, evaporated to dryness, and lyophilized. Each residue is analyzed by thin layer chromatography on silica gel (F254, E. Merck, Darmstadt, Germany) using 9:1 or 3:1 chloroform:methanol and *Micrococcus luteus* as the detecting organism in the bioautogram.

Similar residues, as shown by tlc, are pooled. The following pooled fractions are thus obtained:

| Pooled Fractions | Weight (g.) |
|---|---|
| (1) A6888C "rich" | 1.03 |
| (2) A6888C/A6888X | 0.91 |
| (3) A6888X | 0.64 |
| (4) A6888A (cirramycin B) | 3.43 |
| (5) A6888F (cirramycin A₁) | 1.10 |
| Total | 7.11 |

The fraction shown by tlc to be rich in A6888C (1.03 g from Example 2) is pooled with similar material (0.61 g.) obtained from four 100-L. fermentations using the fermentation and recovery methods described above. The pooled material (1.64 g.) is dissolved in chloroform and loaded onto silica gel (Quantum LP-1) dry packed in a 4 ft.×1 in. stainless steel HPLC column. The column is then eluted at 200–250 psi via a linear gradient (2 L. each) of from chloroform to chloroform-methanol (9:1, v/v) (each containing 0.01% ethanolamine). Each eluted fraction is monitored by tlc on silica gel (F-254, E. Merck, Darmstadt, Germany) using 9:1 and 3:1 chloroform-methanol. The tlc plates are evaluated by bioautography on agar plates containing *Micrococcus luteus*. Fractions containing A6888C are pooled. After removal of solvent, 0.17 g. of dry product is obtained (90+%, A6888C). To this material is added 1.41 g. of a material, shown to be similar in composition by tlc. The added material is obtained from the chromatographic purification of crude material recovered from other large-scale fermentations after CCD using the methods described in Example 2. The combined material (1.54 g.) is rechromatographed as above-described, to give A6888C (0.39 g.) and A6888X (0.139 g.), as shown by tlc.

The physical data obtained by analysis of A6888C, A6888X, cirramycin A₁ (A6888F) and cirramycin B (A6888A) are given below:

A. Elemental Analysis

|  |  | Calculated | Found |
|---|---|---|---|
| A6888C: | C | 62.43% | 61.94 |
|  | H | 8.64 | 8.49 |
|  | N | 1.97 | 2.62 |
|  | O | 26.96 | 26.95 |
| A6888X: | C | 62.25% | 61.02% |
|  | H | 8.90 | 8.52 |
|  | N | 1.96 | 2.18 |
|  | O | 26.89 | 28.28 |
| A6888A: | C | 62.62 | 62.79 |
|  | H | 8.32 | 8.37 |
|  | N | 1.97 | 1.94 |
|  | O | 27.09 | 26.9 |

B. Thin layer chromatography
    tlc plate: F254 silica gel (E. Merck)
    systems: (a) chloroform-methanol, 9:1 (v/v)
            (b) chloroform-methanol, 3:1 (v/v)
    Detecting organism for bioautograms: *Micrococcus luteus*

| Factor | $R_f$ |
|---|---|
| A6888A | 0.51 (9:1) |
|  | 0.86 (3:1) |
| A6888C/A6888X | 0.14 (9:1) |
|  | 0.60 (3:1) |
| A6888F | 0.03 (9:1) |
|  | 0.24 (3:1) |

C. Molecular weight
    (by field desorption mass spectrometry)
    A6888A: 710 (M+1)    m/e = 597
               709 (M+)     m/e = 113
    A6888C: 712 (M+1)    A6888X: 714 (M+1)
               m/e = 596      m/e = 409
               m/e = 407

D. Circular Dichromism
    A6888A: Absorption at 240 nm and 298 nm
    A6888C and A6888X: Absorption at 240 nm E. Ultraviolet Absorption
    A6888A: $\lambda_{max}$ 240 nm
    A6888C: $\lambda_{max}$ 240 nm
    A6888X: $\lambda_{max}$ 240 nm F. $C^{13}$ NMR - chemical shifts (a) A6888A:
| | |
|---|---|
| 14.8 ppm | (C-6″ methyl) |
| 211.0 | (C-4″ carboxyl) |
| 202.8 | (C-18 aldehyde) |
| 200.4 | (C-9 carbonyl) |
| 122.8 | (C-10 double bond) |
| 150.9 | (C-11 double bond) |
| 173.1 | (C-1 carbonyl of lactone) |

(b) A6888C:
| | |
|---|---|
| 16.8 ppm | (C-6″ methyl) |
| 67.3 | (C-4″ hydroxyl) |
| 202.7 | (C-18 aldehyde) |
| 200.3 | (C-9 carbonyl) |
| 122.9 | (C-10 double bond) |
| 151.0 | (C-11 double bond) |
| 173.4 | (C-1 carbonyl of lactone) |

(c) A6888X:
| | |
|---|---|
| 17.2 ppm | (C-6″methyl) |
| 67.2 | (C-4″ hydroxyl) |
| 60.6 | (C-18 primary alcohol) |
| 201.5 | (C-9 carbonyl) |
| 122.9 | (C-10 double bond) |
| 150.7 | (C-11 double bond) |
| 173.4 | (C-1 carbonyl of lactone) |

G. NMR - chemical shifts (a) A6888A:
| | |
|---|---|
| 9.73 ppm | (aldehyde proton) |
| 6.59 | (C-11 double bond proton) |
| 6.39 | (C-10 double bond proton) |
| 2.53 | (C-3′ N-methyls) |
| 1.41 | (C-12 methyl) |
| 4.28 | (C-1′ anomeric proton) |

(b) A6888C:
| | |
|---|---|
| 9.72 ppm | (aldehyde proton) |
| 6.59 | (C-11 double bond proton) |
| 6.4 | (C-10 double bond proton) |
| 2.52 | (C-3′ N-methyls) |
| 1.42 | (C-12 methyl) |
| 4.24 | (C-1′ anomeric proton) |

(c) A6888X:
| | |
|---|---|
| 6.58 ppm | (C-11 double bond proton) |
| 6.4 | (C-10 double bond proton) |
| 2.52 | (C-3′ N-Methyls) |
| 1.42 | (C-12 methyl) |
| 4.32 | (C-1′ anomeric proton) |

EXAMPLE 3

The ability of the compounds of Formula II (A6888C and A6888X) to inhibit the growth of selected pathogenic microorganisms is demonstrated and evaluated in standard test procedures. The results of disc-plate tests are set forth in Table 1 where activity is measured by the size (diameter in mm.) of the observed zone of inhibition. The results of agar-dilution tests are shown in Table 2 where activity in measured by the value of the minimum inhibitory concentration (MIC) which is the amount of substance (μg/ml) required to inhibit the growth of the organism. The results of in vivo tests to evaluate effectiveness against experimental bacterial infections in mice are given in Table 3 where activity is measured by the $ED_{50}$ value [the dose in mg./kg. required to cure 50% to the test animals; see W. Wick et al., J. Bacterial., 81, 233 (1961)]. The MIC values of A6888C and A6888X against selected anerobic bacteria are shown in Table 4. Tables 1, 2, 3, and 4 also give the results of the testing of the A6888 complex as comparisons.

TABLE 1

| | Disc-Plate Zone Sizes (mm) | | |
|---|---|---|---|
| Bacteria | A6888 complex 100 μg Discs | A6888C 100 μg Discs | A6888X 300 μg Discs |
| S. Aureus (3 strains) | 26.8 | 24 | 27 |
| S. pyogenes C203 Group D Streptococcus | 23 | 20 | 24.2 |
|  | 22 | 20 | 22.5 |
| S. pneumoniae I | 30 | 35 | 36 |
| E. coli Ec-14 | 13 | 10.2 | 14 |
| P rettgeri PR-2 | 8.3 | 8 | 8.6 |
| K. pneumoniae KL-14 | 9.3 | 0 | 11.3 |
| Sh. flexneri SH-4 | 13.8 | 18 | 12.5 |
| S. typhosa SA-12 | 10 | 9.9 | 8.8 |

TABLE 2

| Bacteria | MIC (μg/ml) | | |
|---|---|---|---|
| | A6888 Complex | A6888C | A6888X |
| S. aureus 3.55 | <0.4 | 1.0 | 32 |
| S. aureus 3074 | 0.78 | 2 | >128 |
| S. faecalis X-66 | 1.56 | 4 | 16 |

TABLE 3

| Therapy in Experimental Mouse Infections | | | |
|---|---|---|---|
| Mouse Infection | ED$_{50}$ Values (mg/kg × 2) | | |
| | A6888 Complex | A6888C | A6888X |
| S. aureus 3055 | >70 | 5.0 | >70 |
| S. pyogenes C203 | 12.7 | 4.65 | >70 |
| S. pneumoniae I | >70 | not done | >70 |

TABLE 4
SUSCEPTIBILITY OF ANAEROBIC BACTERIAL ISOLATES*

| Anaerobic Bacteria | MIC (μg/ml) | | |
|---|---|---|---|
| | A6888 complex | A6888C | A6888X |
| Actinomyces israelii W855 | <0.5 | 4 | 8 |
| Clostridium perfringens 81 | <0.5 | 2 | 16 |
| Clostridium septicum 1128 | <0.5 | 2 | 16 |
| Eubacterium aerofaciens 1235 | <0.5 | 2 | 8 |
| Peptococcus asaccharolyticus 1302 | <0.5 | 2 | 8 |
| Peptococcus prevoti 1281 | <0.5 | 32 | >64 |
| Peptostreptococcus anaerobius 1428 | <0.5 | 2 | 16 |
| Peptostreptococcus intermedium 1264 | 2 | 16 | 8 |
| Propionibacterium acnes 79 | 1.0 | 2 | 1.0 |
| Bacteroides fragilis spp. fragilis 111 | <0.5 | 64 | 64 |
| Bacteroides fragilis ssp. fragilis 1877 | <0.5 | 16 | 64 |
| Bacteroides fragilis ssp. fragilis 1936B | <0.5 | 32 | 64 |
| Bacteroides fragilis ssp. thetaiotaoimicron 1438 | 1.0 | 8 | 16 |
| Bacteroides melaninogenicus 1856/28 | 8 | 64 | 64 |
| Bacteroides melaninogenicus 2736 | <0.5 | 32 | 64 |
| Bacteroides vulgatis 1211 | 4 | 8 | 32 |
| Bacteroides corrodens 1874 | 1.0 | 32 | 32 |
| Fusobacterium symbiosum 1470 | <0.5 | 4 | 128 |
| Fusobacterium necrophorum 6054A | 2 | 16 | 128 |

*MIC Determined by the agar-dilution method. Endpoints were read after 27 hours incubation.

EXAMPLE 4

As an alternative to the procedure of Example 2, Antibiotic A6888A (cirramycin B) can be recovered from fermentation broths as follows:

To the whole fermentation broth (179 L.) obtained from two fermentations, is added one-half volume of methanol (90 L.). The resulting mixture is filtered in the presence of filter aid. The separated filtrate is adjusted to pH 6.5–7.0 and extracted with an equal volume of ethyl acetate (235 L.). The ethyl acetate phase is concentrated to an aqueous medium (20 L.) which is extracted twice with one-half volume (10 L.) of ethyl acetate. The combined ethyl acetate phases are concentrated (1.9 L.), and the concentrate is extracted with 0.1 N HCl (1 L.). Adjustment of the pH of the acid extract to 7.0 with 5 N NaOH forms a precipitate of cirramycin B. Yield: 3.15 g.

What is claimed:

1. A method for producing cirramycin A$_1$, cirramycin B, or a compound of the formula:

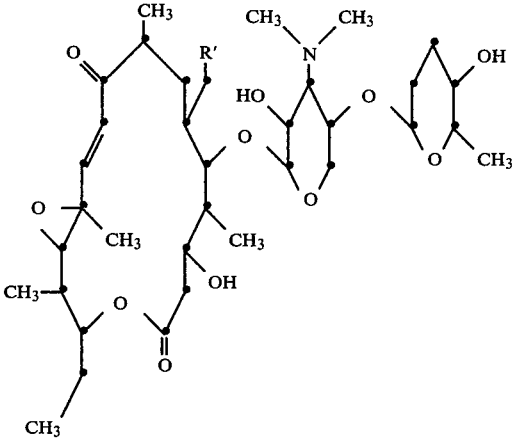

wherein:
(a) R' is

—CH, and
(b) R' is —CH$_2$OH;

or a non-toxic, pharmaceutically acceptable acid addition salt thereof comprising cultivating Streptomyces flocculus NRRL 11459 in a culture medium containing assimilable sources of carbon, nitrogen, and inorganic salt under submerged aerobic conditions until a substantial amount of each compound is produced.

2. A method as defined in claim 1 for producing the compound wherein R$^1$ is —CH.

3. A method as defined in claim 1 for producing the compound wherein R$^1$—CH$_2$OH.

4. A method as defined in claim 1 for producing cirramycin A$_1$.

5. A method as defined in claim 1 for producing cirramycin B.

6. A method as defined in claim 2, 3, 4 or 5 wherein the compound is isolated in substantially pure form.

* * * * *